US010420862B2

(12) United States Patent
Sharma et al.

(10) Patent No.: US 10,420,862 B2
(45) Date of Patent: Sep. 24, 2019

(54) IN-SITU FORMING FOAMS FOR TREATMENT OF ANEURYSMS

(75) Inventors: Upma Sharma, Somerville, MA (US); Gregory Zugates, Chelmsford, MA (US); Rany Busold, Medford, MA (US); Toby Freyman, Waltham, MA (US)

(73) Assignee: Aresenal AAA, LLC., Watertown, MA (US)

( * ) Notice: Subject to any disclaimer, the term of this patent is extended or adjusted under 35 U.S.C. 154(b) by 807 days.

(21) Appl. No.: 13/532,013

(22) Filed: Jun. 25, 2012

(65) Prior Publication Data

US 2012/0265287 A1   Oct. 18, 2012

Related U.S. Application Data

(63) Continuation-in-part of application No. 13/209,020, filed on Aug. 12, 2011, which is a continuation-in-part of application No. 12/862,362, filed on Aug. 24, 2010.

(60) Provisional application No. 61/236,314, filed on Aug. 24, 2009, provisional application No. 61/368,095, filed on Jul. 27, 2010, provisional application No. 61/601,151, filed on Feb. 21, 2012.

(51) Int. Cl.
| | |
|---|---|
| *A61F 2/82* | (2013.01) |
| *A61L 31/14* | (2006.01) |
| *A61L 31/06* | (2006.01) |
| *A61L 31/18* | (2006.01) |
| *A61M 25/00* | (2006.01) |

(52) U.S. Cl.
CPC .............. *A61L 31/146* (2013.01); *A61L 31/06* (2013.01); *A61L 31/14* (2013.01); *A61L 31/141* (2013.01); *A61L 31/18* (2013.01); *A61L 2400/06* (2013.01); *A61L 2430/36* (2013.01); *A61M 25/007* (2013.01)

(58) Field of Classification Search
CPC ........................................................ A61F 2/82
USPC ............................................. 623/1.15, 1.35
See application file for complete search history.

(56) References Cited

U.S. PATENT DOCUMENTS

| | | | |
|---|---|---|---|
| 4,764,377 | A | 8/1988 | Goodson |
| 5,364,627 | A | 11/1994 | Song |

(Continued)

FOREIGN PATENT DOCUMENTS

| | | |
|---|---|---|
| WO | WO-1994/18956 A1 | 9/1994 |
| WO | WO-2003/020161 A2 | 3/2003 |

(Continued)

OTHER PUBLICATIONS

Rhee et al, "Treatment of type II endoleaks with a novel polyurethane thrombogenic foam; Induction of endoleak thrombosis and elimination of intra-aneurysmal pressure in the canine model" *Journal of Vascular Studies*, 42:2, 321-328, Aug. 2005.

(Continued)

*Primary Examiner* — Matthew W Schall

(57) ABSTRACT

Systems, methods and kits relating to in-situ forming polymer foams for the treatment of aneurysms are disclosed. The systems include an insertable medical device and an in-situ forming foam that is formed from a polymer that reacts in an aqueous environment. When used to treat an aneurysm, the foam is placed into contact with at least a portion of an exterior surface of the medical device and/or the tissue surface of the aneurysm.

20 Claims, 4 Drawing Sheets

(56) References Cited

U.S. PATENT DOCUMENTS

| | | |
|---|---|---|
| 5,538,735 A | 7/1996 | Ahn |
| 5,567,612 A | 10/1996 | Vacanti et al. |
| 5,569,528 A | 10/1996 | Van der Loo et al. |
| 5,725,568 A | 3/1998 | Hastings |
| 5,800,476 A | 9/1998 | Piunti |
| 5,842,477 A | 12/1998 | Naughton et al. |
| 5,922,340 A | 7/1999 | Berde et al. |
| 5,944,341 A | 8/1999 | Kimura et al. |
| 5,980,927 A | 11/1999 | Nelson et al. |
| 6,002,968 A | 12/1999 | Edwards |
| 6,086,911 A | 7/2000 | Godbey |
| 6,156,842 A | 12/2000 | Hoenig |
| 6,214,370 B1 | 4/2001 | Nelson et al. |
| 6,382,526 B1 | 5/2002 | Reneker et al. |
| 6,495,124 B1 | 12/2002 | Samour |
| 6,520,425 B1 | 2/2003 | Reneker |
| 6,524,608 B2 | 2/2003 | Ottoboni et al. |
| 6,596,296 B1 | 7/2003 | Nelson et al. |
| 6,655,366 B2 | 12/2003 | Sakai |
| 6,676,953 B2 | 1/2004 | Hexamer |
| 6,676,960 B2 | 1/2004 | Saito et al. |
| 6,685,956 B2 | 2/2004 | Chu et al. |
| 6,685,957 B1 | 2/2004 | Bezemer et al. |
| 6,689,374 B2 | 2/2004 | Chu et al. |
| 6,695,992 B2 | 2/2004 | Reneker |
| 6,712,610 B2 | 3/2004 | Abdennour et al. |
| 6,716,449 B2 | 4/2004 | Oshlack et al. |
| 6,737,447 B1 | 5/2004 | Smith et al. |
| 6,753,454 B1 | 6/2004 | Smith et al. |
| 6,821,479 B1 | 11/2004 | Smith et al. |
| 6,855,366 B2 | 2/2005 | Smith et al. |
| 6,858,222 B2 | 2/2005 | Nelson et al. |
| 6,861,142 B1 | 3/2005 | Wilkie et al. |
| 6,861,570 B1 | 3/2005 | Flick |
| 6,913,760 B2 | 7/2005 | Carr et al. |
| 7,029,495 B2 | 4/2006 | Stinson |
| 7,033,603 B2 | 4/2006 | Nelson et al. |
| 7,033,605 B2 | 4/2006 | Wong |
| 7,048,913 B2 | 5/2006 | Hexamer |
| 7,048,946 B1 | 5/2006 | Wong et al. |
| 7,074,392 B1 | 7/2006 | Friedman et al. |
| 7,135,194 B2 | 11/2006 | Birnbaum |
| 7,172,765 B2 | 2/2007 | Chu et al. |
| 7,198,794 B1 | 4/2007 | Riley |
| 7,214,506 B2 | 5/2007 | Tatsumi et al. |
| 7,235,295 B2 | 6/2007 | Laurencin et al. |
| 7,285,266 B2 | 10/2007 | Vournakis et al. |
| 7,309,498 B2 | 12/2007 | Belenkaya et al. |
| 7,323,190 B2 | 1/2008 | Chu et al. |
| 7,462,362 B2 | 12/2008 | Kepka et al. |
| 7,678,366 B2 | 3/2010 | Friedman et al. |
| 7,737,060 B2 | 6/2010 | Strickler et al. |
| 7,765,647 B2 | 8/2010 | Smith et al. |
| 7,799,965 B2 | 9/2010 | Patel et al. |
| 7,803,395 B2 | 9/2010 | Datta et al. |
| 7,824,699 B2 | 11/2010 | Ralph et al. |
| 7,959,616 B2 | 6/2011 | Choi et al. |
| 7,959,848 B2 | 6/2011 | Reneker et al. |
| 7,959,904 B2 | 6/2011 | Repka |
| 7,997,054 B2 | 8/2011 | Bertsch et al. |
| 9,044,580 B2 | 6/2015 | Freyman et al. |
| 2001/0021873 A1 | 9/2001 | Stinson |
| 2002/0176893 A1 | 11/2002 | Wironen et al. |
| 2003/0017208 A1 | 1/2003 | Ignatious et al. |
| 2003/0068353 A1 | 4/2003 | Chen et al. |
| 2003/0171773 A1 | 9/2003 | Carrison |
| 2003/0195611 A1 | 10/2003 | Greenhalgh et al. |
| 2004/0030377 A1 | 2/2004 | Dubson et al. |
| 2004/0034408 A1* | 2/2004 | Majercak et al. ............ 623/1.15 |
| 2004/0076661 A1 | 4/2004 | Chu et al. |
| 2004/0217503 A1 | 11/2004 | Grinshpun et al. |
| 2005/0033163 A1 | 2/2005 | Duchon et al. |
| 2005/0042293 A1 | 2/2005 | Jackson et al. |
| 2005/0106211 A1 | 5/2005 | Nelson et al. |
| 2005/0165480 A1 | 7/2005 | Jordan |
| 2005/0175662 A1 | 8/2005 | Hunter et al. |
| 2005/0276841 A1 | 12/2005 | Davis et al. |
| 2006/0008419 A1* | 1/2006 | Hissink et al. ................ 424/45 |
| 2006/0153815 A1 | 7/2006 | Seyda et al. |
| 2006/0276831 A1 | 12/2006 | Porter et al. |
| 2006/0293743 A1 | 12/2006 | Andersen et al. |
| 2007/0087027 A1 | 4/2007 | Greenhalgh et al. |
| 2007/0155273 A1 | 7/2007 | Chu et al. |
| 2007/0176333 A1 | 8/2007 | Greene et al. |
| 2007/0232169 A1 | 10/2007 | Strickler et al. |
| 2007/0293297 A1 | 12/2007 | Schugar |
| 2008/0053891 A1 | 3/2008 | Koops et al. |
| 2008/0132936 A1 | 6/2008 | Sawhney et al. |
| 2008/0269126 A1 | 10/2008 | Ballance et al. |
| 2008/0281350 A1 | 11/2008 | Sepetka et al. |
| 2009/0155326 A1 | 6/2009 | Mack et al. |
| 2010/0131002 A1* | 5/2010 | Connor et al. ................ 606/200 |
| 2010/0249913 A1 | 9/2010 | Datta et al. |
| 2010/0291182 A1 | 11/2010 | Palasis et al. |
| 2010/0318108 A1 | 12/2010 | Datta et al. |
| 2011/0184530 A1 | 7/2011 | Datta et al. |
| 2011/0237994 A1 | 9/2011 | Russ et al. |
| 2012/0107439 A1 | 5/2012 | Sharma et al. |

FOREIGN PATENT DOCUMENTS

| | | |
|---|---|---|
| WO | 2007/0005140 A1 | 1/2007 |
| WO | WO-2007/052042 A2 | 5/2007 |
| WO | WO-2008/013713 A2 | 1/2008 |
| WO | WO 2011/007352 | 1/2011 |

OTHER PUBLICATIONS

Kanani et al., "Review on Electrospul Nanofibers Scaffold and Biomedical Applications", Trends Biomater, Artif, Organs, vol. 24(2), pp. 93-115, (Aug. 2010).

Biomedical Structures, Glossary: Common Biomedical Textile Terms (accessed Oct. 12, 2011), 1-11 pgs.

Bini, T.B. et al., "Electrospun poly(L-lactide-co-glycolide) biodegradable polymer nanofiber tubes for peripheral nerve regeneration", Nanotechnology, 15, 2004, 1459-1464.

Jose, Moncy V. et al., "Fabrication and characterization of aligned nanofibrous FLGA/Collagen blends as bone tissue scaffolds", Polymer, 50, 2009, 3778-3785.

Liao, Yiliang et al., "Preparation, characterization, and encapsulation/release studies of a composite nanofiber mat electrospun from an emulsion containing poly(lactic-co-glycolic acid)", Polymer, 49, 2008, 5294-5299.

Wei, Kai et al., "Emulsion Electrospinning of a Collegen-like Protein/PLGA Fibrous Scaffold: Empirical Modeling and Preliminary Release Assessment of Encapsulated Protein", Macromolecular Bioscience, 11, 2011, 1526-1536.

Sy, Jay C. et al., "Emulsion as a Menas of Controlling Electrospinning of Polymers", Advanced Materials, 21, 2009, 1814-1819.

International Search Report dated Jan. 18, 2011 for International Application No. PCT/US2010/057010 (3pgs).

International Search Report dated Jan. 5, 2012 for International Application No. PCT/US2011/47615 (3 pgs).

International Search Report dated Jan. 2, 2013 for International Application No. PCT/US2012/062732.

International Search Report dated Jun. 18, 2013 for International Application No. PCT/US2013/046281 (4 pgs).

* cited by examiner

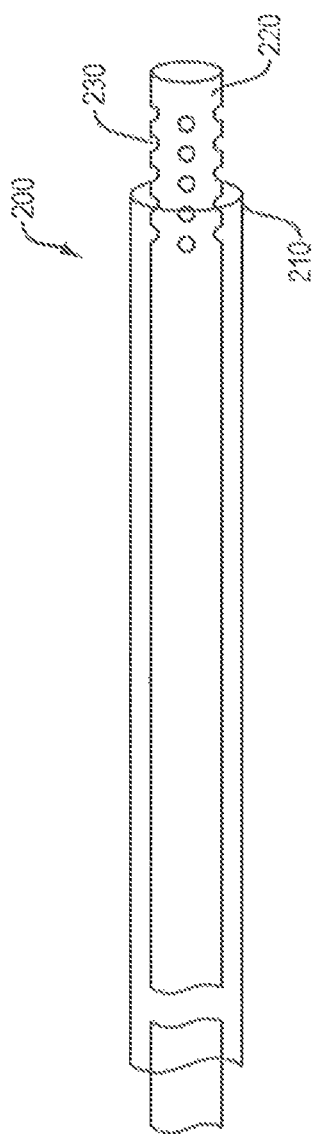
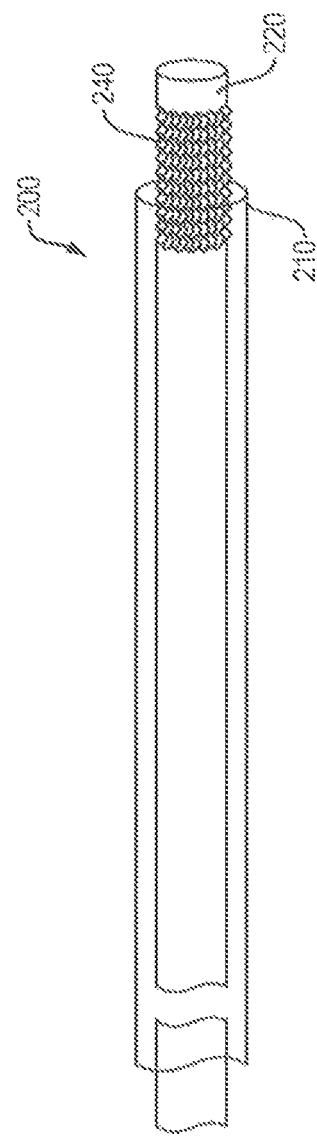
FIG. 4A
FIG. 4B

IN-SITU FORMING FOAMS FOR TREATMENT OF ANEURYSMS

CROSS-REFERENCE TO RELATED APPLICATIONS

This application is a continuation-in-part of U.S. application Ser. No. 13/209,020 filed Aug. 12, 2011 and titled "In-situ Forming Hemostatic Foam Implants," which is a continuation-in-part of U.S. application Ser. No. 12/862,362, filed Aug. 24, 2010 and titled "Systems and Methods Relating to Polymer Foams," which claims priority to U.S. Provisional Patent Application Ser. No. 61/236,314 filed Aug. 24, 2009 and titled "Systems and Methods Relating to Polymer Foams," each of which are incorporated by reference herein for all purposes. This application also claims priority to U.S. Provisional Patent Application Ser. No. 61/601,151 filed Feb. 21, 2012 and titled "In Situ Forming Implants to Treat Endoleaks," which is incorporated by reference herein for all purposes.

FIELD OF INVENTION

Systems and methods relating to polymer foams for the treatment of aneurysms are generally described.

BACKGROUND

Early stabilization of body fluid loss can be important in the treatment of wounds and bleeding tissues. For example, many injuries are treatable if effective hemorrhage control and operative surgical intervention are undertaken rapidly. In many situations, however, immediate access to surgical care is not available. Internal wounds and bleeding sites may be particularly difficult to treat in such situations, as traditional treatment techniques (e.g., application of pressure to stop bleeding, etc.) are difficult to implement with such wounds.

Although the use of polymers in the treatment of wounds is well known in the art, previous materials and methods for treating wounds with polymers have suffered from a variety of drawbacks. For example, many polymers irritate skin and/or internal tissues. Moreover, many polymers lack suitable mechanical properties to be useful inside the body; polymers that are too stiff may lead to discomfort or further injury, while polymers that are too soft may fail to provide adequate support for internal tissues. In addition, polymers can be difficult to place within internal wounds or bleeding sites that may have complex shapes and geometries.

One clinical application in which polymers have been used to control bleeding is in the treatment of aneurysms. Generally, an aneurysm is an abnormal widening or ballooning of a portion of a blood vessel due to weakness in the vessel wall. If left untreated, aneurysms can grow large and rupture, causing internal bleeding which is often fatal. Two locations in which aneurysms are commonly found are in the abdominal aorta and the brain.

Abdominal aortic aneurysms ("AAAs") are conventionally treated by surgical removal or by endovascular repair. If the AAA is surgically repaired, a major incision is made in the abdomen or chest to access and remove and/or repair the aneurysm, and the aneurysmal segment of aorta is replaced or supplemented with a tubular graft of synthetic material such as Dacron® or Teflon®. If instead it is treated by endovascular aneurysm repair ("EVAR"), the AAA is accessed via catheter using minimally invasive techniques rather than through an open surgical incision. A graft or stent-graft is delivered through the catheter and self-expands as it is expelled from the catheter to bridge the aneurysm to form a stable channel for blood flow. FIG. 1 shows an aneurysm 110 in an abdominal aorta 115 after treatment by the placement of a stent-graft 150, as is known in the art. With the increased use of EVAR in recent years, a higher incidence of endoleaks has been observed. An endoleak results from blood that is still able to access the aneurysm sac 116 after placement of the graft or stent-graft. Such a leak could be caused by an insufficient seal at the ends of the graft (referred to as a "type I" leak), retrograde flow into the aneurysm from collateral vessels (a "type II" leak), a defect in the graft (a "type III" leak), and flow through any porosity in the graft (a "type IV" leak). Such endoleaks represent a significant possible drawback to EVAR procedures as they could lead to aneurysm expansion or rupture. Endoleaks are less of a concern following surgical repair of AAA, but the surgical procedure is significantly more invasive and has higher mortality and morbidity. Thus, an improved EVAR device and system which address endoleaks would provide a significant improvement in patient care.

It has recently been proposed (Rhee et al., "Treatment of type II endoleaks with a novel polyurethane thrombogenic foam: Induction of endoleak thrombosis and elimination of intra-aneurysmal pressure in the canine model," *J. Vasular Surgery* 2005, 42(2): 321-8), incorporated herein by reference, to use a pre-formed polyurethane foam in the aneurysm sac following an EVAR procedure. The authors found that the use of such a foam resulted in a reduction of intra-aneurysmal pressure to a level that was indistinguishable from control aneurysms that had no endoleak. Such a pre-formed foam, however, cannot be shaped in-situ to conform to the configuration of the aneurysm sac. As such, the authors were required to make use of numerous foam implants to achieve the reported results.

Likewise, it has been proposed in U.S. Publication No. 2009/0287145, incorporated herein by reference, to introduce a foam material into an aneurysm. The foam is compressible to allow for injection and then expands from its compressed configuration and hardens in-situ. The foam itself, however, is pre-formed prior to injection into the aneurysm.

SUMMARY OF THE INVENTION

Systems, methods and kits relating to in-situ forming polymer foams for the treatment of aneurysms are provided.

In one aspect, the present invention comprises a system comprising an insertable medical device and an in-situ forming foam. The medical device comprises a structure having a first end, a second end, and an exterior surface between the first and second ends. The in-situ forming foam comprises a polymer that reacts in the presence of an aqueous environment (e.g., blood, water, etc.) to generate a gas and form the foam, and when used in the system to treat an aneurysm, is in contact with at least a portion of the exterior surface of the medical device and/or the tissue surface of the aneurysm.

In another aspect, the present invention comprises a method for treating an aneurysm within a patient. The method comprises the steps of placing a medical device within the aneurysm such that the medical device spans the aneurysm, and inserting an in-situ forming foam between an exterior surface of the medical device and the tissue surface of the aneurysm. The in-situ forming foam is formed from a polymer that reacts in the presence of an aqueous environment to generate a gas.

In another aspect, the present invention comprises a kit that includes a medical device and a polymer formulation. The medical device comprises a structure having a first end, a second end, and an exterior surface between the first and second ends. The polymer formulation reacts in the presence of blood or water to generate a gas and form a foam.

In another aspect, the present invention comprises delivery catheters and related methods for the delivery of formulations that are adapted to react in the presence of an aqueous environment to generate a gas and form a foam.

In another aspect, the present invention comprises instructions for treating an aneurysm. The instructions instruct a healthcare provider to place a medical device such as a stent-graft within the aneurysm and to insert an in-situ forming foam between an exterior surface of the medical device and the tissue surface of the aneurysm, where the in-situ forming foam comprises a polymer that reacts in the presence of an aqueous environment to generate a gas and form a foam.

In other aspects, the invention includes foams, compositions, formulations, products, kits, and systems that are useful for providing the foams and performing the methods described above.

The present invention offers advantages not previously known in the art. For example, the polymers of the invention can be deployed into an aneurysm sac without requiring specific knowledge of the aneurysm configuration while nonetheless creating conformal contact within the sac and thus minimizing and/or preventing endoleaks. Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 4 shows systems for the delivery of in-situ forming foams, in accordance with embodiments of the present invention.

DETAILED DESCRIPTION

Figure 1:
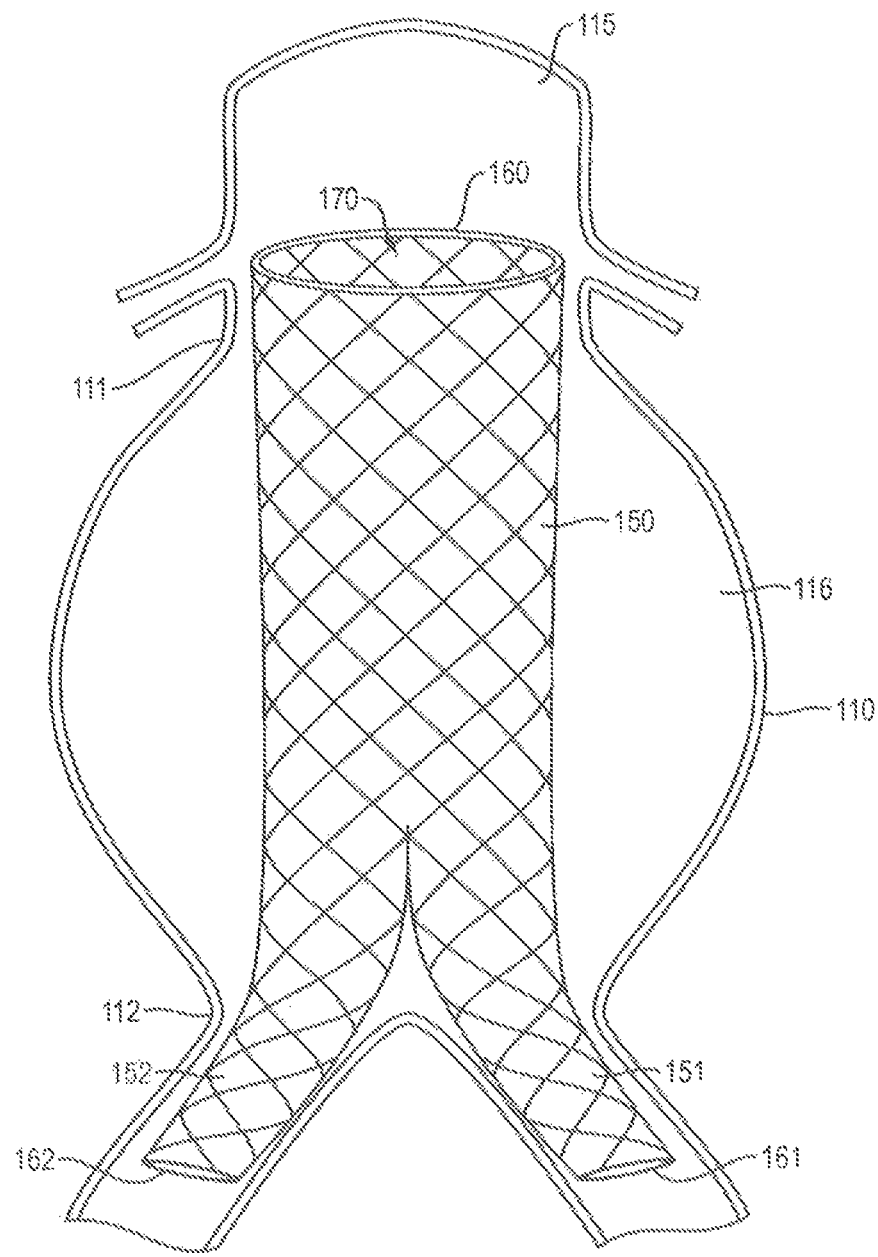
FIG. 1 shows the conventional placement of a stent-graft within an abdominal aortic aneurysm.

Systems, methods and kits related to the treatment of aneurysms using in-situ forming polymer foams are generally described. As will be recognized by those skilled in the art, although the present invention is described with specific reference to the use of in-situ forming foams within aneurysm sacs, the foams of the present invention may be applied to any body cavities such as abdominal, pelvic, and cardio thoracic cavities, and placed in contact with, for example, tissue, injured tissue, internal organs, etc. As used herein, "aneurysm sac" refers to the sac formed by the localized dilation in a blood vessel at an aneurysm site.

The polymer foams of the present invention are formed "in-situ." That is, the foams are formed by the reaction of polymer(s) in an aqueous environment simultaneously with, or shortly after, delivery to an aneurysm sac. This is in contrast to pre-formed foams, which are formed prior to the time that they are delivered into the body. The foamed polymers of the present invention may be capable of exerting a pressure on an internal surface of an aneurysm sac and thus prevent or limiting movement of a bodily fluid (e.g., blood, etc.) and/or prevent or limit endoleaks as previously described. Such in-situ forming foams preferably expand to fill the aneurysm sac volume, resulting in conformal contact with the aneurysm walls and penetration into blood vessels and other lumens opening into the sac. The location of such vessels is not always obvious with standard imaging technique, such that the ability to seal such vessels with the foams and methods of the present invention without requiring visualization is a unique advantage of the present invention. Also, the foams are formed by the reaction of polymers in-situ to yield gas generation and expansion, which allows for the use of minimal polymer materials and allows the resulting foam to push through fluid, including actively flowing blood, to provide conformal contact with surrounding tissue. Finally, an additional advantage of the present invention is the added structure and anchoring sites within collateral vessels following formation of a fully formed foam. Such anchoring sites may provide for the anchoring or stabilizing of an implanted graft or stent-graft, thus preventing migration thereof. These and other factors are important distinctions and advantages of in-situ forming foams over systems and methods that make use of pre-formed foams.

The polymer foams of the present invention may possess attributes that make them particularly suitable for use within the body. For example, the foams of the present invention are biocompatible and may be either biodegradable or biostable. In some instances, the polymers may be sufficiently elastic to allow for body movement while being sufficiently stiff to support body tissues. In some embodiments, the composition may be adjusted so that it wets tissues effectively. Furthermore, pendant groups may be attached that allow for the targeted adhesion of polymer to tissues or injured tissues. Functionalization of the polymer used to form the foam may also lead to covalent bonding of the foam to a surface inside the aneurysm sac, which may aid, for example, in preventing dislocation of the foam within the cavity. In addition, the polymers may comprise entities that allow for the degradation of the polymer foam via an external stimulus such as UV radiation, heat, etc. The polymers and/or foams formed therefrom may also be capable of interacting with contrast agents, allowing for the visualization of an aneurysm sac. This interaction may be permanent or temporary. These and other aspects of the foams used in the present invention are more fully described herein.

Examples of in-situ forming foams and methods of using such foams for the treatment of aneurysms are now provided.

FIG. 1 shows the placement of a stent-graft within an abdominal aortic aneurysm, as is known in the art. Although the present invention is described with specific reference to the treatment of AAAs, it should be appreciated that it is applicable to the treatment of any aneurysm, such as those in the descending thoracic aorta, in the peripheral vasculature, and in the brain. Any graft, stent-graft, balloon, or the like insertable into an aneurysm sac is suitable for use in the current invention as the insertable medical device, such as the ANEURX AAADVANTAGE®, TALENT®, and ENDURANT® stent-grafts manufactured by Medtronic, Inc. Such stent-grafts typically include a metallic scaffold supporting a synthetic material, such as a woven or unwoven mesh or fabric that is placed over, within or around the scaffold. The stent-graft expands into place after being delivered through an EVAR procedure, as is known in the art. Although the stent-graft shown in FIG. 1 is a so-called "branched" or "bifurcated" stent-graft because it branches into legs 151, 152, it should be recognized that unbranched stent-grafts (i.e., stent-grafts that are not bifurcated into legs) are suitable for use in the present invention. Also suitable for use in the present invention are fenestrated stent-grafts, as are known in the art.

Regardless of whether a branched or unbranched stent-graft is used, the stent-graft will include a first end 160, second end 161 and/or 162, and a lumen 170 extending there between. The first end 160 of stent-graft 150 is secured to a first end 111 of aneurysm 110. As used herein, a graft or stent-graft is said to be "secured" to the end of an aneurysm if it is held into contact with surrounding tissue, such as by friction fit without the use of any securing means or alternatively with the use of such securing means such as sutures, adhesives, or other suitable securing means. The second end 161 and/or 162 of stent-graft 150 is secured to a second end 112 of aneurysm 110 to span the aneurysm and form a stable channel for blood flow within abdominal aorta 115.

As an alternative to stent-grafts, the present invention may be used with tubular grafts that are unsupported by stent scaffolds. As another alternative, the present invention may be used with one or more inflatable balloons, which are temporarily inserted into the patient as the medical device, around which the in-situ forming foam is delivered.

Figure 2:
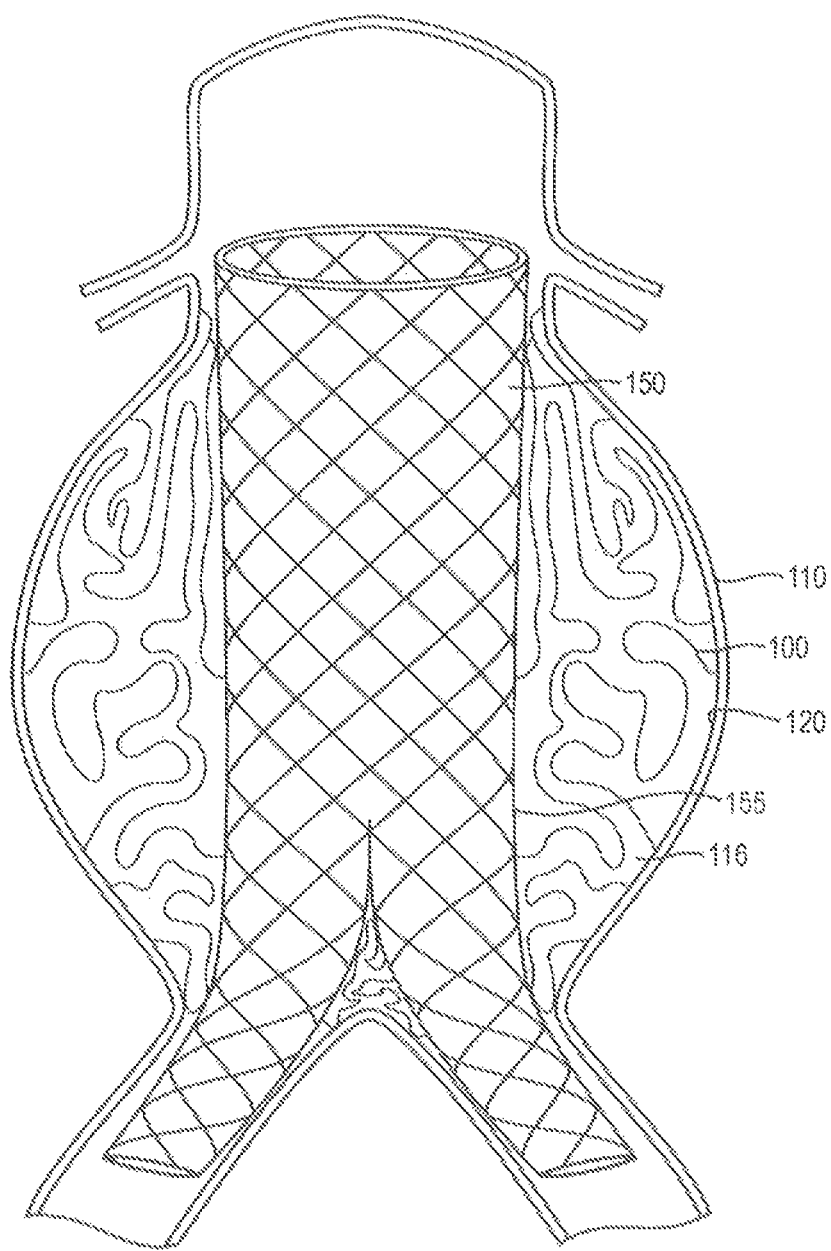
FIG. 2 shows an embodiment of the present invention in which an in-situ forming foam has been placed in the space between a stent-graft and an aneurysm sac.

In accordance with the present invention, after the graft, stent-graft or balloon is placed within an aneurysm, an in-situ forming foam is inserted between an exterior surface 155 of the medical device (such as stent-graft 150) and a tissue surface 120 of aneurysm 110. In a preferred embodiment as shown in FIG. 2, the in-situ forming foam 100 may substantially fill the aneurysm sac 116. Because of the in-situ forming nature of the foam 100, it preferably expands to contact substantially all tissue surfaces defining the aneurysm sac 116, including penetrating into blood vessels and any other lumens opening into the aneurysm. Alternatively, the foam 100 may only partially fill the aneurysm sac 116. In various embodiments, the foam 100 is placed into contact with the exterior surface 155 of stent-graft 150, the tissue surface 120 of aneurysm 110, both of these surfaces, or neither of these surfaces. The exterior surface 155 of the medical devices of the present invention are preferably generally substantially solid, meaning that they include some porosity but are sufficiently solid to prevent substantial quantities of foam from flowing there-through.

As used herein, a "foam" refers to an article comprising a plurality of cells (i.e., volumes) that are at least partially surrounded by a material comprising a polymer, and is preferably biocompatible and nonabsorbable. The cells within the foam may be open or closed. The cells within the foam may be any suitable size, such as one or more nanometers, microns, millimeters, or centimeters. The cell size may be substantially uniform throughout the foam, such as where at least 90% of the cells are the same order of magnitude in size, or may have a wide size distribution spanning two or more orders of magnitude. In some embodiments, the polymer foam may comprise at least 10 cells, at least 100 cells, at least 1000 cells, at least 10,000 cells, or more. The foam is formed in-situ substantially commensurately with the delivery of a foam-forming polymer into the aneurysm sac, whereupon it reacts with blood present within the sac, or with saline, water or other suitable fluid delivered together with the polymer, or with another aqueous environment. Such fluid may pre-exist at the delivery site (as in the case of blood) in a so-called "one-part system," or it may be delivered to the site concurrently with the polymer or it may be pre-mixed with the polymer shortly before delivery in so-called "two-part systems." In such two-part systems, the fluid delivered with (or pre-mixed with) the polymer is preferably saline.

The polymer material can comprise a plurality of polymers which can be, for example, cross-linked to each other in the process of forming a polymer foam. In some embodiments, the polymer material comprises fluid polymers in the substantial absence of a carrier fluid. In other instances, the plurality of polymers in the polymer material are suspended in a carrier fluid (e.g., a liquid suspension medium, etc.) or dissolved in a carrier fluid to create a homogeneous phase. The term "polymer" is given its ordinary meaning in the art, and is used to refer to a molecule that includes a plurality of monomers. Included within the definition of "polymer" are "pre-polymers," which are a subclass of polymers that are characterized by reactive groups in the polymer chain. Such pre-polymers are of particular use in the present invention because the reactive groups in such polymers help drive the in-situ forming foam reaction. In some embodiments, a polymer may comprise fewer than about 100, fewer than about 50, fewer than about 25, or fewer than about 10 monomer units. In some embodiments, a polymer may comprise between about 2 and about 100, between about 2 and about 50, between about 2 and about 25, between about 5 and about 50, or between about 5 and about 25 monomer units. The polymers within the polymer material can comprise a variety of functional groups that allow the polymers to, for example, cross-link to each other, attach to tissue or other material within the aneurysm sac, interact with agents in the bloodstream of the subject (e.g., imaging agents, cross-linking agents, etc.), among other functionalities.

In some embodiments, the polymers within the polymer material may cross-link within the aneurysm sac. The term "cross-linking" is used to refer to the process whereby a pendant group on a first polymer chain may react with a second polymer chain (e.g., a pendant group on the second polymer) or other molecule or molecules to form a covalent or ionic bond joining the two polymers. Polymers that can undergo cross-linking can comprise straight chains, branched chains having one or more arms (i.e., multi-arm chains), or mixtures of these. In some cases, the polymer (branched and/or non-branched) may contain reactive side chains and/or reactive terminal groups (i.e., groups at the end of a polymer chain), and cross-linking may involve reactions between the side chains, between terminal groups, and/or between a side chain and a terminal group. In some instances, the polymer material may be substantially free of polymers that comprise reactive groups on terminal monomers. In other cases, the polymer material may comprise a substantial amount of polymers with reactive groups on terminal monomers. In some embodiments (e.g., in some cases in which branched polymers are employed) a relatively large percentage of the cross-linking reactions (e.g., at least about 70%, at least about 80%, at least about 90%, at least about 95%, at least about 99%, or substantially all of the cross-linking reactions) can occur between terminal reactive groups.

Cross-linking may commence via a variety of mechanisms. In some embodiments, polymer may cross-link once the polymer contacts moisture (e.g., water, blood, aqueous solutions, etc.), for example, within an aneurysm sac. Cross-linking may be achieved via acrylate, methacrylate, vinyl, cinnamic acid, or acrylamide groups in some embodiments. Such groups may be cross-linked via the application of ultraviolet radiation and can be used in conjunction with an external foaming agent. In some instances, a cross-linking initiator may be introduced into the subject in which the aneurysm sac is located (e.g., via the bloodstream, via a separate container in the delivery system such that the initiator and the polymer do not mix before delivery, etc.) to initiate cross-linking of the polymer. For example, a free radical initiator, such as eosin or 2,2-dimethoxy-2-phenylacetophenone, can be used to initiate cross-linking of polymers bearing acrylate, methacrylate, or vinyl groups. Other examples of reactive groups on polymer chains that can be paired to produce cross-linking include, but are not limited to, hydroxyls and isocyanates, amines and NHS-esters, thiols and maleimides, azides and alkynes (i.e. "click chemistry"), acid chlorides and alcohols, and in a preferred embodiment, isocyanates and polyols. It may be desirable, in some embodiments, to keep these paired chemicals separate until they are introduced into the aneurysm sac to prevent unwanted cross-linking outside the aneurysm sac. For example, the polymer may include azide functional groups, and alkynes can be introduced to the aneurysm sac from a container separate from the container used to introduce the polymer. In some embodiments, these chemistries are also employed in conjunction with an external foaming agent. As the polymer material cross-links, its viscosity may be increased. In some cases, the cross-linking proceeds until a cellular solid material (e.g., a solid elastomeric foam) is formed.

In some embodiments, a gas is formed from the reaction of the polymer supplied to the aneurysm sac. For example, in some embodiments, the foaming step comprises reacting one or more pendant groups on the polymer or cross-linked product to form a gaseous product. The gas-producing pendant groups may react upon contact with another material in the aneurysm sac. For example, in some cases, the gas producing groups may react upon contact with moisture in the aneurysm sac. In some cases, the gas-producing pendant groups may react with a chemical supplied to the aneurysm sac separately from the polymer material (e.g., via the bloodstream, via an external source separate from the polymer material source, etc.). In some embodiments, the gas-producing pendant groups on the polymer chain may react with another component that is supplied to the aneurysm sac. In some embodiments, the polymer or cross-linked product may comprise $CO_2$-producing groups. $CO_2$ producing groups are preferred due to the biocompatibility of $CO_2$ and high solubility of $CO_2$ in blood. Examples of $CO_2$-producing groups include, but are not limited to, isocyanate groups, carbonates, bicarbonates, and carbamates. Such groups may produce $CO_2$ gas when reacted with an acid, for example. In some cases, the $CO_2$-producing group may include an N-hydroxysuccinimide carbonate, illustrated below:

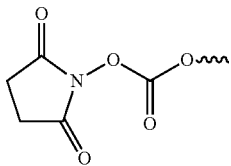

$CO_2$-producing groups may include, in some cases, imidazole carbamates, as illustrated below:

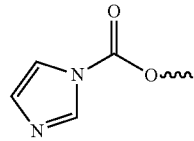

As noted above, in some embodiments, the foaming and cross-linking steps occur substantially simultaneously. In some cases, the foaming and cross-linking steps may occur substantially simultaneously, but remain independent of each other. For example, the polymer material may cross-link by reacting with water in the aneurysm sac, and, at substantially the same time, gas may be introduced to the polymer material from an external container. In another embodiment, a first material containing gas generating groups may produce gas by contact with a second agent (e.g., water in the body, water supplied separately, or chemical additive), while contact or interaction with a third material leads to crosslinking. For example, at the time of delivery, polymer A with isocyanate groups can be mixed with water and polymer B, in which the former causes the generation carbon dioxide to foam the material and polymer B can contain hydroxyl groups that react with isocyanates on polymer A to form a crosslinked network between polymers A and B.

The foaming and cross-linking steps may be, in some cases, part of the same reaction process. For example, one or more reactions may produce a gaseous by-product which serves as the supply of gas to form the polymer foam, but concurrently leads to the generation of new functional groups that enable crosslinking. The gaseous by-product can be trapped within the polymer and coalesce to form bubbles. As the reaction progresses, the formation, growth and expansion of the gas bubbles can expand the polymer volume and force it into interstitial areas of the aneurysm sac. As the polymer cross-links, a three-dimensional foam can be formed within the aneurysm sac. The volume expansion and cross-linking can serve to coat and form a seal with surfaces of the aneurysm sac, and optionally provide internal compression, which may be useful, for example, in stopping bleeding. In addition, such a reaction scheme can be combined with an external supply of gas (e.g., $CO_2$ in an external container) to increase the amount of gas contained in the polymer or a cross-linked product of the polymer.

All of the foaming mechanisms described herein may occur before any substantial cross-linking has occurred or during cross-linking of the polymer material or a cross-linked product of the polymer material. For example, in some cases, an external gas may be introduced into and dispersed within a polymer material that has not substantially cross-linked. The polymer material may then cross-link around the bubbles to form the foam. In such cases, the viscosity and surface tension of the polymer material can be chosen such that the material is able to retain bubbles within the volume without the need for cross-linking. In another embodiment, a surfactant can be added to the polymer material to create a formulation that retains gas bubbles without the need for crosslinking. In some embodiments, at least some cross-linking may occur before the gas is introduced to the polymer material, and the gas is dispersed within a partially cross-linked polymer material that has not completely solidified to form a foam.

In a preferred embodiment, the foam used in the present invention is a polyurethane foam formed in-situ from a one-part formulation consisting of an isocyanate-functionalized polymer. The polyurethane foam is preferably a poly (urethane urea). Optionally, this formulation additionally contains multiple polymer species, catalysts, surfactants, chain extenders, crosslinkers, pore openers, fillers, plasticizers, and diluents. The polymer formulation also may include a pro-coagulant such as thrombin, kaolin, glass, chitosan, or other hemostatic agent; and preferably a visualization material such as contrast media and radiopaque agents that render the resultant foam visible through fluoroscopy or other visualization techniques. In the presence of water, blood or other aqueous environment, the polymer reacts to form a foam. Preferably, the quantity of fluid and the isocyanate content control the volume expansion such that foaming is minimized when fluid is and/or isocyanate are depleted from the aneurysm. The viscosity of this polymer formulation is preferably less than 10,000 cP and more preferably less than 5,000 cP. With respect to density and expansion, foams have been developed having densities between 10 and 1,000 kg/m$^3$, or having expansions of between 1 and 95 fold. When used in the present invention, foams with no or low expansion (e.g., 1.01 to 1.25×) consume at least some of the blood volume in the target space during polymer reaction and replace it with the newly-formed foam. If more polymer is applied than needed, the excess amount will not react to form a foam. In such a system, a pressure-feedback system may be used to monitor complete fill of the aneurysm because the reaction will stop when all blood/water is consumed by the reaction. The product will slightly expand to fill the target space without the risk of over-expansion and generation of undesirable pressures. The target maximum pressure is up to about 170 mmHg or about 50 mmHg above systolic blood pressure. In general, increasing the water and/or isocyanate content of the formulation tends to increase the volume expansion. Without wishing to be bound to theory, it is believed that this is due to increased blowing and $CO_2$ evolution.

Polymers used to form the foams of the present invention are preferably formed by the reaction of di- and/or polymeric, multifunctional isocyanates with polyols. A strict or true polymer can be formed by a stoichiometric 2:1 NCO:OH ratio. A quasi-polymer may be more preferable in which NCO:OH ratios greater than 2:1 are used so that the excess NCO lowers the viscosity and increases the NCO weight percent of the polymer phase. Isocyanates of preference include hexamethyline diisocyanate (HDI), toluene diisocyanate (TDI), xylene diisocyanate, methylene diphenyl diisocyanate (MDI), lysine isocyanate (LDI), isophorone diisocyanate, isocyanate-functionalized polymer, polymeric isocyanate (with functionality preferably between 2.0-3.0), or mixtures thereof. Preferred polyols include polyether, polybutadiene, polysiloxane or any non-hydrolytically and non-enzymatically degradable polymer backbone terminated with hydroxyl functionalities. Even more preferable are polyol blends or copolymers that include both hydrophobic and hydrophilic segments. Such hydrophilic polyols and their corresponding polymers may enable faster uptake of water into the polymer and thus a faster, and more complete foaming reaction compared to more hydrophobic polymers.

In an embodiment, polymers are designed to foam to a pre-determined, maximum volume based on the isocyanate content, hydrophilicity and catalyst. The isocyanate content is controlled by the isocyanate:polyol ratio used during polymer synthesis, with the residual, unreacted isocyanate setting the maximum possible $CO_2$ and hence volume that can be generated. Both the hydrophilicity and catalyst(s) type/level influence that amount and rate of water penetration, $CO_2$ evolution, and crosslinking kinetics.

Cross-linking and/or foaming may be achieved, in some instances, using isocyanate chemistry. Isocyanate groups are relatively unstable when exposed to water and moisture. Exposure of isocyanate groups to water or moisture (or other compounds) can lead to the decomposition of the groups, cross-linking of polymers to which they are attached, and release of carbon dioxide, as shown below for a model lysine isocyanate:

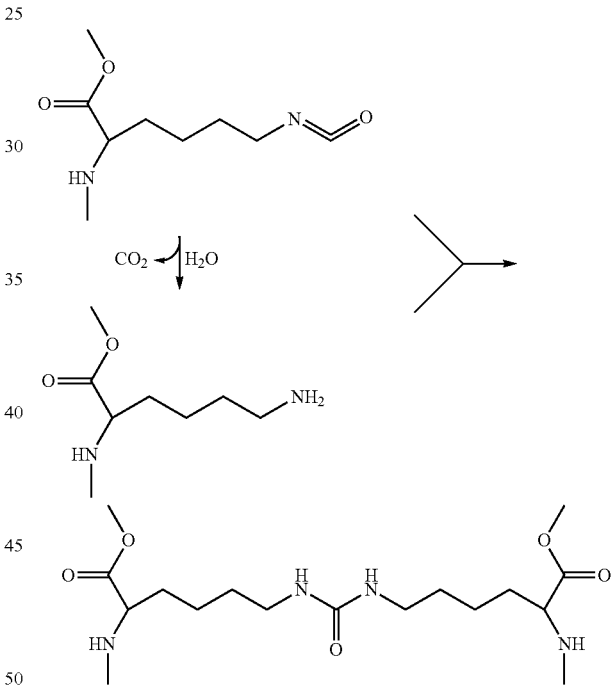

In the mechanism above, the isocyanate is partially hydrolyzed to produce an amine, which can react with native, non-hydrolyzed isocyanates, as shown above. Not wishing to be bound by any theory, a cross-linked structure can be produced because the rate of the amine-isocyanate reaction may be on the order of or faster than the rate of isocyanate hydrolysis, and inter-chain reactions occur between these functional groups to ultimately form a cross-linked structure. The isocyanates on the polymer can also react with amine groups of the tissue (e.g. lysines in proteins), which can form a covalent bond with the tissue to further strengthen the seal at sites in which fluid is being lost (e.g., at bleeding sites). In addition, the isocyanate hydrolysis reaction produces $CO_2$, enabling simultaneous cross-linking and gas production in a single-reaction scheme.

In certain preferred embodiments, polyurethane foams are generated by cross-linking polyols with multifunctional isocyanates. Polyols suitable for use in such embodiments include polyether- and polybutadiene-based polyols. Polyols of particular interest include polypropylene glycol (PPG) and polyethylene glycol (PEG), as well as random and block copolymers thereof. Also suitable for use are polycarbonates, polybutadienes, polysiloxanes and polyesters. Diols, triols, and tetrols are most preferred, but multifunctional polyols with any suitable number of arms may be used. Molecular weights between 100 and 10,000 Da are preferable, with molecular weights up to 6,000 Da being most preferred, and blends of polymers with different molecular weights, degrees of branching, and composition are often used. Commercial polymers of particular interest include polypropylene glycols (425, 1200 Da), polyethylene glycols (200, 400, 600, 1000, 2000, 3000 Da), Pluracol products (355, 1135i, 726, 816), Arch Poly-G 30-240, Poly-G 76-120, Poly-G 85-29, trimethylolpropane ethoxylate (450, 1014 Da), pentaerythritol ethoxylate (797 Da), UCON 75-H-1400, UCON 75-H-9500, dipropylene glycol, diethylene glycol, tripropylene glycol, triethylene glycol, tetrapropylene glycol, and tetraethylene glycol.

In some instances, it may be advantageous to position isocyanate groups in the polymer so that it is accessible for hydrolysis and cross-linking, without inhibiting binding to the tissue (e.g., damaged blood vessels). In one set of embodiments, a lysine group in the targeting peptide can be converted to an isocyanate by reaction with diphosgene. In some instances, the isocyanate and peptide chemistries can be completely decoupled by modifying a fraction of the side chains with peptide while the balance are modified with isocyanate.

The polymer that is foamed to form the in-situ forming foams described herein may be formed using a variety of chemistries. In some embodiments, the polymer comprises a synthetic polymer. As used herein, a "synthetic polymer" refers to a polymer that is a product of a reaction directed by human interaction. For example, synthetic polymers can include polymers synthesized by reactions of natural or synthetic monomers or combinations thereof that are directed by human interaction. The formation of synthetic polymers can also include chain elongation of natural or synthetic polymers. In some embodiments, the synthetic polymer is not found in nature. In other cases, the synthetic polymer can be found in nature, but the polymer is synthesized via human interaction (e.g., in a laboratory setting). In some embodiments, the polymer may comprise a poly alpha-hydroxy acid. In some cases, the polymer may comprise a polyester. In some cases, the polymer may comprise a polyether-polyester block copolymer. In some cases, the polymer may comprise a poly(trimethlyene carbonate). In some embodiments, the backbone of the polymer can exclude at least one of polynucleotides, proteins, and polysaccharides.

In some embodiments, the polymer foam is formed by cross-linking a condensation polymer of a polyol and a polyacid. The terms "polyol" and "polyacid" are given their standard meanings in the art, and are used to refer to compounds comprising at least two alcohol groups and at least two acidic groups, respectively. Examples of polyols suitable for use in forming the condensation polymer used to form the polymer foams described herein include, but are not limited to, glycerol, polyethylene glycol, polypropylene glycol, polycaprolactone, vitamin B6, erythritol, threitol, ribitol, arabinitol, xylitol, allitol, altritol, galactritol, sorbitol, mannitol, iditol, lactitol, isomalt, and maltitol, wherein the functional groups present on the polyol are optionally substituted. Examples of polyacids suitable for use in forming the condensation polymer used to form the polymer foams described herein include, but are not limited to, succinic acid, fumaric acid, a-ketoglutaric acid, oxaloacetic acid, malic acid, oxalosuccinic acid, isocitric acid, cis-aconitic acid, citric acid, 2-hydroxy-malonic acid, tartaric acid, ribaric acid, arabanaric acid, xylaric acid, allaric acid, altraric acid, galacteric acid, glucaric acid, mannaric acid, dimercaptosuccinic acid, oxalic acid, malonic acid, succinic acid, glutaric acid, adipic acid, pimelic acid, suberic acid, azelaic acid, sebacic acid, malic acid, or vitamin B5, wherein the functional groups present on the polyacid are optionally substituted.

The properties of the polymer used to form the polymer foam may be tailored to achieve a desired result. For example, in some embodiments, the viscosity of the polymer is tailored such that the polymer formulation is better able to permeate the aneurysm sac and create conformal contact with the sac wall and/or the medical device placed within the aneurysm. An overly viscous polymer formulation may require excessive pressure to deploy within the aneurysm sac. In addition, an overly viscous polymer formulation may inhibit the polymer from accessing interstitial spaces. An overly low-viscosity polymer formulation might be difficult to contain the material to the injured site or may be displaced by the flow of a bodily fluid. One of ordinary skill in the art will be able to produce the desired viscosity for a given polymer type by, for example, adjusting the molecular weight of the polymer. In some embodiments, the viscosity and the molecular weight are related through a power law. The molecular weight of a polymer may be adjusted by, for example, controlling the time of the polymerization reaction used to generate the polymer. In some embodiments, the molecular weight of the polymer is between about 1000 and about 10,000 g/mol or between about 1200 and 6000 g/mol. The viscosity of the formulation may be adjusted by, for example, adding diluents such as any suitable low molecular weight, low viscosity compound, examples of which include triacetin, propylene carbonate, tetraethylene glycol dimethyl ether, dimethyl esters of diacids (e.g., diethyl malonate, dimethyl adipate), dimethyl sulfoxide, and oils (vegetable, olive, castor, etc.). In some embodiments, the polymer is amorphous or semi-crystalline with a glass transition temperature ($T_g$) below room temperature. Such properties yield, in some cases, polymers with sufficiently low viscosities that they can be dispensed from an external container via pressure-driven flow.

In some embodiments, properties or composition of the polymer may be chosen to achieve a desired hydrophilicity or hydrophobicity. The hydrophilicity of the polymer may be selected, in some instances, such that the surfaces (e.g., tissue surfaces) within an aneurysm sac are appropriately wetted. Generally, a material with increased hydrophilicity will have a greater tendency to wet soft tissues surfaces and to react more quickly because of better mixing with blood. However, the polymer and resulting polymer foam may be, in some cases, somewhat hydrophobic such that they do not dissolve into biological fluids. Appropriately hydrophilic polymers are capable of conformally wetting interior surfaces of an aneurysm sac while remaining contained within the cavity. In some embodiments, the composition of the polymer may be selected to achieve a desired hydrophilicity. For example, in some embodiments, the chain length of a monomer used to synthesize the polymer can be varied to change hydrophilicity. As a specific example, the carbon chain length between carbonyl groups of a diacid monomer can be varied from between two and eight aliphatic carbons, producing a range of hydrophilicity in the resulting polymer.

In some embodiments, the polymer foams described herein may have favorable mechanical properties. In some embodiments, the polymer foams are elastomeric. The term "elastomer" as used herein, refers to a polymer that can return to the approximate shape from which it has been substantially distorted by an applied stress. In some cases, the elastomeric polymer foams described herein may comprise a polymer having a bulk modulus of between about 0.05 MPa and about 10 MPa; 0.05 MPa and about 100 MPa; and 0.05 MPa and about 500 MPa. Elastomeric polymers may be particularly suitable for use in making polymer foams because they are capable sustaining stress without permanently deforming, while providing adequate support for body organs and tissues.

The time required to form the polymer foam after exposure of the formulation to the aneurysm sac and the final mechanical and physicochemical properties of the polymer foam can depend on such factors as the composition of the polymer and its hydrophobicity, the density of pendant groups (e.g., cross-linking groups), relative positions of the pendant groups (e.g., cross-linking groups), and other factors.

In some embodiments, the polymer or polymer foam may be biodegradable. As used herein, "biodegradable" describes materials that are capable of degrading down to oligomeric or monomeric species under physiological or endosomal conditions. The phrase "physiological conditions," as used herein, relates to the range of chemical (e.g., pH, ionic strength) and biochemical (e.g., enzyme concentrations) conditions likely to be encountered in the intracellular and extracellular fluids of tissues. In some embodiments, the physiological pH ranges from about 7.0 to 7.4. In some embodiments, biodegradable materials are not hydrolytically degradable but can be fully degraded via enzymatic action to fully degrade. In some cases, biodegradable materials are hydrolytically or enzymatically degradable, or combinations thereof. In some embodiments, the polymer or polymer foam is biodegradable, but it does not biodegrade over the time scale in which it is located within an aneurysm sac. In such cases, the polymer foam can remain structurally stable while being inserted into the aneurysm sac, while ensuring that any remnants of the polymer foam that remain within the aneurysm sac after removal can be biodegraded.

The polymeric foams described herein may be used, in some embodiments, to prevent or limit the movement of a bodily fluid within the aneurysm sac, relative to an amount of movement of bodily fluid that would occur under essentially identical conditions in the absence of the polymer foam. "Essentially identical conditions," in this context, means conditions that are similar or identical other than the presence of the polymer foam. For example, otherwise identical conditions may mean that the aneurysm sac is identical, the conditions within the cavity are identical, but where no polymer foam is located within the aneurysm sac. In some embodiments, the polymer foam may be used to reduce the movement of blood or other bodily fluid within an aneurysm sac.

The movement of bodily fluids may be prevented or limited over a relatively long period of time. In the primary embodiment, the foam forms a permanent hemostatic implant within the aneurysm sac.

In some cases, the movement of bodily fluids may be prevented or limited via the application of pressure. For example, the formation of the polymer foam may involve volumetric expansion of the polymer. In some embodiments, the expansion of the polymer may result in the application of a pressure to a surface within the aneurysm sac.

In some cases, the movement of bodily fluids may be prevented or limited due to a physical seal created between the aneurysm wall or collateral vessel walls (e.g. inferior mesenteric artery, lumbar arteries) and the surface of the foam. This seal may be due to chemical bonding between the tissue surface and foam and/or the highly conformal contact of the foam with the tissue surfaces combined with the foam's tendency to induce coagulation of blood. In addition, the foam may penetrate collateral vessels within the aneurysm sac to further limit blood flow into the sac. Preferably in-situ expansion of the foam leads to penetration of these collateral vessels by less than about 2 cm. In some cases, the polymer may be designed to cross-link quickly, for example, by tailoring the polymer to have functional groups that crosslink quickly, by adding catalysts, or by other known means. Suitable catalysts for use in embodiments of the present invention include amine based compounds, preferably tertiary amines, triethylenediamine (TEDA, DABCO, DABCO 33-LV), bis(2-dimethylaminoethyl)ether (Niax A1), trimethylaminoethyl-ethanolamine, 1,2-dimethylimidazole. In addition, the pores of the foam can trap blood and allow it to coagulate in stagnant areas.

In addition to gas-forming pendant groups, other active agents may also be included as pendant groups on the polymer. For example, the polymer foam can include groups used to stimulate desirable cellular responses such as fibroplasia, angiogenesis and epithelialization. In some embodiments, the polymer or polymer foam may be covalently bonded to a surface within the aneurysm sac, for example, through a pendant group.

In some embodiments, the polymer or cross-linked product may comprise at least one pendant group that can bind to tissue or injured tissue (e.g., inflamed tissue, bleeding tissue, a wound site, etc.) within the aneurysm sac. The binding of the pendant groups to the tissue or injured tissue can be covalent or non-covalent. The tissue or injured tissue may comprise one or more molecules that would not be present in or near uninjured tissue as is the case, for example, when subendothelial surfaces are exposed. By including such pendant groups, a polymer or cross-linked product could be made that selectively binds to tissue or injured tissue, in comparison to uninjured tissue. Such binding may limit or prevent the movement of bodily fluid within the aneurysm sac, in some embodiments. Examples of chemicals that may be targeted by pendant groups on the polymer or polymer foam include, for example, von Willebrand Factor, collagen (e.g., collagen I and IV), a fibroblast growth factor, laminin, elastin, localized coagulation factors in their activated form (e.g., fibrin, thrombin, factor Xa, etc.), among others. Example of types of pendant groups that may be bound to the polymer or polymer foam for such uses include, for example, peptides, carbohydrates (e.g., oligosaccharide sequences), aptamers.

In addition to targeting tissues or injured tissues, pendant groups may be used to stabilize tissue or injured tissue. For example, pendant groups (e.g., $CO_2$-forming groups) may covalently bond to tissue, in some cases, which may lead to the sealing of one or more openings within an aneurysm sac. Such binding can aid in limiting or preventing the movement of bodily fluid within the aneurysm sac, in some cases. In some embodiments, the concentration of isocyanate in the polymer or a cross-linked product can affect the extent to which binding between the polymer and tissue occurs. Specifically, increasing the isocyanate levels can serve to increase and reinforce the polymer-tissue contact area, potentially producing a stronger and longer-lasting seal. Increasing the level of isocyanate in the polymer can also increases the crosslink density, potentially resulting in a more rigid material that may break more easily at the polymer-tissue interface (e.g., when the body is moved). Therefore, the concentration of isocyanate may be selected, in some cases, to balance between these two effects.

In another embodiment, the polymer properties are selected such that minimal covalent binding of the foam to tissue is observed. The foam, however, can be bound to tissue by different non-covalent forces, such as electrostatic, Van der Waals, or capillary. Minimal covalent binding of foam to tissue can facilitate easy foam removal and prevent adhesions, such as abdominal adhesions, during the healing process.

In some cases, non-isocyanate pendant groups may be used to stabilize the polymer-tissue interface. For example, the polymer may comprise aldehyde reactive groups, which can be used, for example to bind tissue proteins. Aldehyde groups may be attached by, for example, attaching ethanolamine to the polymer, followed by oxidizing the pendant hydroxyl group to form an aldehyde group. In some instances, pendant groups that selectively bind to fibrin may be used to stabilize the clot-polymer interface. In addition, pendant groups may be selected that compete with plasminogen and its activators for fibrin binding sites, blocking the activation of fibrinolytic cascade.

In some instances, a drug may be delivered to the aneurysm sac with the polymer. In some embodiments, the polymer may comprise a drug. For example, a drug (or a plurality of particles containing one or more drugs) may be dispersed within the polymer. Example of such drugs include, but are not limited to, antifibrinolytic compounds (e.g., aminocaproic acid, tranexamic acid, etc.), anti-fibrotic compounds, antimicrobial compounds (e.g., antibiotics), anti-inflammatory compounds, analgesics, pro-coagulant compounds, statins, growth factors, and vasoconstrictors. Drugs that comprise amine groups may, in some cases, be isolated from isocyanates within the polymer, for example, to prevent unwanted reaction during the cross-linking step. Isolation can be achieved by encapsulating drugs into secondary particles and loading them into the polymer at the time of delivery to the aneurysm sac. In addition, encapsulation may be used to release the drugs at a controlled rate. In some embodiments, a drug may be incorporated into a fiber, which may be included in the polymer. The drug release rate from the fiber can be controlled by varying composition and structure (e.g., thickness or other dimension, presence of sheath) of fiber. For example, the fiber can be designed to deliver an initial burst release shortly after the deployment of the polymer, followed by sustained delivery (e.g., over the time period in which the polymer foam will be left in the aneurysm sac).

The polymer may be combined with a second agent (and, optionally, a third agent, fourth agent, etc.), in some cases, before or after the polymer is transported to the aneurysm sac. The second agent may comprise, for example, a compound that accelerates at least one of cross-linking and foaming, relative to a rate of at least one of cross-linking and foaming that would have occurred in the absence of the second agent. For example, in some embodiments, the second agent may comprise an amine (e.g., a polyamine). The amine compound may serve to increase the rate at which the polymer cross-links, which may also reduce the amount of time required to reduce or eliminate the movement of a fluid (e.g., blood) within the aneurysm sac. The second agent may comprise, in some cases, at least one of lysine, spermine, spermidine, hexamethylenediamine, polylysine, polyallylamine, polyethylenimine, and chitosan. In some cases, the second reagent may comprise a carbonate or a bicarbonate which may be used, for example, to produce $CO_2$ gas in-situ, as described above. In some embodiments, the second reagent can comprise an acid which may be used, for example, as a reactant in the $CO_2$-producing reaction. The acid functionality may comprise, for example, a carboxylic acid pendant group attached to a polymer chain or blended with a polymer to form a mixture. In some cases, the second reagent can be native in the body (e.g., bicarbonate in the blood). In other cases, the second agent may originate from outside the aneurysm sac. For example, the second agent may be, for example, supplied to the aneurysm sac along with the polymer.

In some embodiments, the combination of the second agent with the polymer produces a polymer foam with significantly different mechanical properties (e.g., elastic modulus, yield strength, breaking strength, etc.) than would have been produced in the absence of the second agent. For example, addition of the second agent may lead to increased cross-linking among polymer molecules, potentially producing a stiffer foam. In another embodiment, the second agent may have a high molecular weight, such that the distance between crosslinks is high, and the resulting foam is softer.

In other embodiments, particles or fibers are included in the foam formulation to result in a composite structure which provides desirable mechanical properties. For example, biocompatible polymer fibers may be included in the unreacted components. These fibers will distribute throughout the foam during in-situ expansion and become part of the structure upon crosslinking. These fibers can provide a more durable, stronger or higher modulus implant. Addition of space filling, highly-compliant particles or fibers may alternately provide a lower modulus, but also more durable implant. Inclusion of fibers which constrain the expansion of the foam may also prevent or limit foam expansion into collateral vessels in the aneurysm sac.

The combination of the second agent with the polymer may, in some embodiments, prevent or limit the flow of blood into the aneurysm sac, relative to an amount of blood flow that would occur under essentially identical conditions in the absence of the second agent. In some embodiments, blood flow may be reduced due to the increased rate of cross-linking or foaming mentioned above. In some cases, the second agent may comprise a pro-coagulant compound (e.g., thrombin, fibrinogen, factor X, factor VII, kaolin, glass, chitosan, or other hemostatic agent).

The second agent may be stored in a container separate from the polymer, for example, to prevent unwanted reaction between the polymer and the second agent outside the aneurysm sac. In some embodiments, a container can be used that keeps the polymer and the second agent separated while stored or transported, but allow for mixing at the outlet nozzle or within the aneurysm sac when the contents are expelled. The outlet nozzle can mix multiple components (>2) including gases in a static or dynamic manner. Examples of static mixers are helical mixers, Low Pressure Drop (LPD) mixers, square element mixer (Quadro), GXF and Interfacial Surface Generator (ISG) mixers. Examples of dynamic mixers are impellers, and rotary static mixers. Nozzles will handle low and high pressure differentials during dispensing. The container may also be designed to mix the components immediately prior to dispensing by breaking the barrier between each of the components and allowing them to mix. Mixing can occur manually such as shaking the canister or chambers can be under vacuum and when the barrier is broken a vortex will be created to mix the components.

In another embodiment, additives can be added to the polymer that absorb heat if generated during the cross-linking reaction. For example, materials in the form of micro or nano-particles, spheres or fibers can absorb the heat by undergoing a phase change (e.g. melting) or glass transition and thereby reduce the heat absorbed by biological tissues. For example, biodegradable fibers made of polycaprolactone can melt at ~60° C., absorbing the generated heat and reducing tissue damage.

In some embodiments, the aneurysm sac can be imaged. The ability to image the aneurysm sac can allow for efficient localization and repair of an injury, stabilization of a wound, etc. In some embodiments, pendant groups on the polymer or polymer foam can be utilized to aid in imaging the aneurysm sac. For example, a contrast agent can be introduced into the blood stream of a subject in which the aneurysm sac is located, and the contrast agent may be capable of selectively binding to pendant groups of the polymer. Examples of contrast agents include, for example, colored, fluorescent, or radio-opaque imaging entities. Examples of radio-opaque imaging entities include, for example, barium-based substances, iodine-based substances, tantalum powder, tantalum oxide powder, tantalum-based substances, and zirconium dioxide. In another embodiment the foam itself provides sufficient radio contrast to surrounding tissues to facilitate visualization. In some embodiments, the contrast agents emit electromagnetic radiation in the near-infrared range (e.g., about 700 to about 1000 nm) upon interacting with the polymer foam. As a specific example, quantum dots (QD) may be used as contrast agents. In some cases, fluorescent organic tags (e.g. fluoroscein isocyanate) or radio-opaque chelating groups (e.g., Gd3+) can be used with appropriate imaging equipment. In another example, the contrast agents listed above may be attached as pendant groups to the polymer or dispersed in the polymer to aid in visualization. In another example, tantalum, titanium or barium sulfate powder may be physically mixed with the polymer for visualization. To provide a time-dependent contrast, the foam may include bio-erodible particles or fibers which include the contrast agent. Following exposure to a physiological environment, the particles or fibers will erode and release the contrast agent which can then be eliminated from the implant site. This can provide implants which become less radio-opaque, for example, over time post delivery. This may be advantageous to users who want to evaluate location of the foam for some time after implantation, but then do not desire to have a radio-opaque foam providing imaging artifacts which limit assessment of surrounding tissues. Preferably the radio-opacity will decrease substantially within three months of implantation.

A variety of mechanisms can be employed to remove polymer or polymer foam from the aneurysm sac or from placement on tissue, if desired. In some embodiments, at least part of the polymer foam is removed via surgical intervention. For example, the polymer foam may be cut out of the aneurysm sac, in some instances. In some cases, surgical intervention may be sufficient to remove the bulk of the polymer foam material (e.g., at least about 80%, at least about 90%, etc.) from the aneurysm sac. The polymer or the pendant groups bonded to the polymer may be selected, in some cases, such that the resulting polymer foam can be removed from an aneurysm sac. In some embodiments that employ a biodegradable polymer or polymer foam, the foam or the remainder of the foam after surgical removal may biodegrade over time. In other embodiments, the foam is permanently implanted in the patient.

In another embodiment drug-loaded objects are incorporated in the foam or gel at or before administration. Incorporation of drug-loaded objects into a polymer during administration is accomplished by those methods known to those skilled in the medical and pharmaceutical formulation arts. Examples of drug-loaded objects include: microspheres, microfibers, core-sheath microfibers, core-sheath nanofibers, nanoparticles, nanospheres, nanofibers or pure particles of drug. Preferably drug is released from these objects over a period of 7 days. More preferably the drug is released up to 14 days. Drug may be released for up to 30 days or longer. Preferably the kinetic release profile for the drug provides approximately the same dose of drug throughout a given period of time.

In certain embodiments, the invention is a polyurethane foam that is formed in-situ from a two-part formulation as previously described. The first part of the formulation includes an isocyanate compound such as hexamethylene diisocyanate (HDI), toluene diisocyanate (TDI), methylene diphenyl diisocyanate (MDI) or a mixture of MDI isomers, polymeric MDI, isocyanate-functionalized polymer, or a polymeric isocyanate having a functionality of preferably between 2.0 and 3.0. The second part of the formulation includes a hydroxyl-functionalized polymer (polyol). The preferred viscosity of the first and second parts of the formulation is 1 to 10,000 cP, and preferably about 1 to about 5,000 cP. The polyol phase optionally has multiple polyol species, catalysts, surfactants, chain extenders, cross-linkers, pore openers, fillers, plasticizers and water. Air, carbon dioxide or other auxiliary blowing agents are optionally entrained into either the isocyanate or polyol phases prior to delivery to the patient or, alternatively, are introduced during delivery as a component of the formulation.

Delivery Systems

Figure 3:
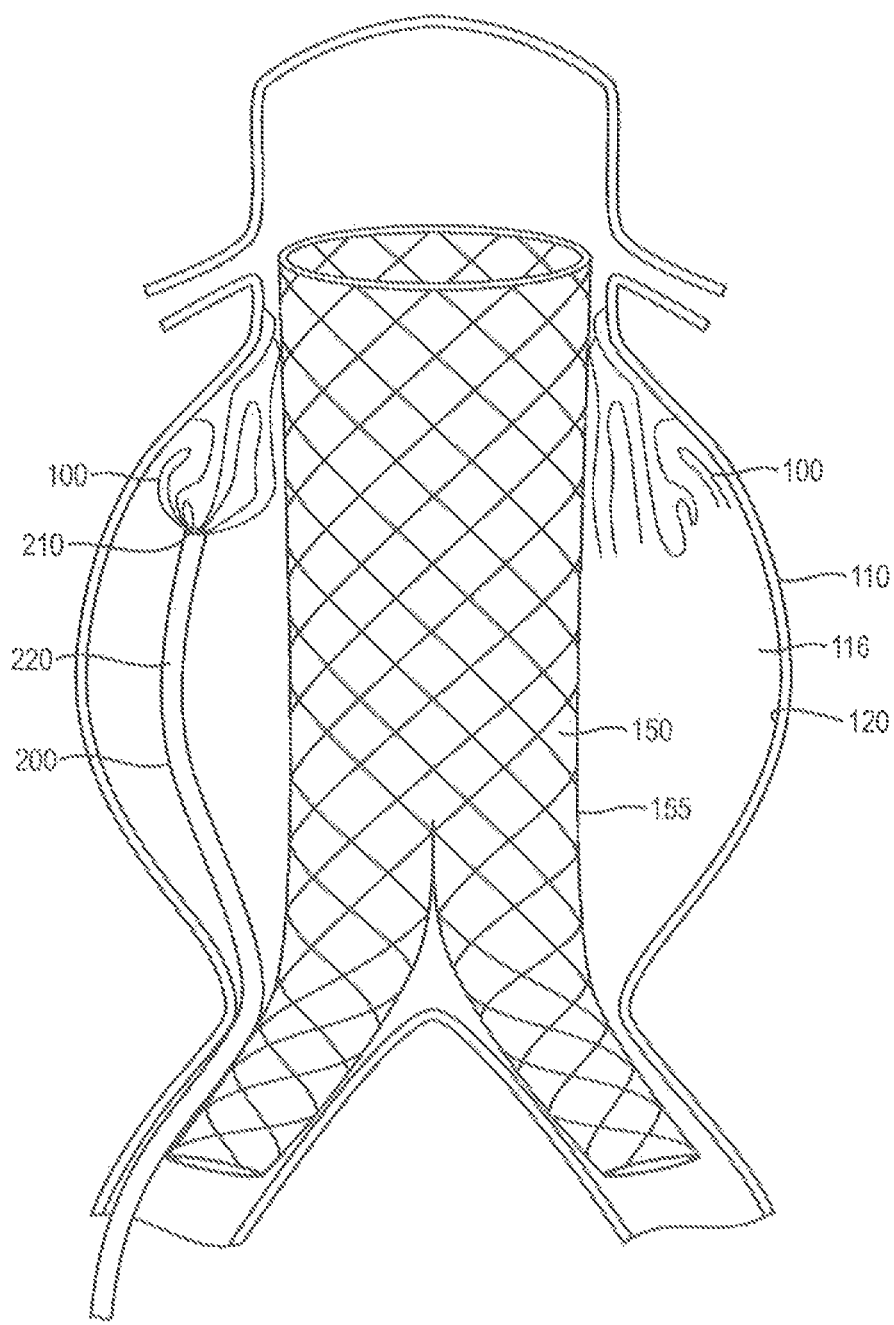
FIG. 3 shows an embodiment of the present invention in which a polymer is delivered into an aneurysm sac and reacts to form an in-situ forming foam.

The in-situ forming foams of the present invention are delivered to an aneurysm site using any suitable delivery means. In one embodiment, the polymer that forms the foam is delivered through a delivery catheter 200, as shown in FIG. 3. The catheter 200 is generally an elongated tube having an open distal end 210 and a lumen 220 extending along the length of the tube. When placed within the aneurysm sac 116, the polymer is extruded from the distal end 210, whereupon it reacts in the presence of blood or other fluid to generate a gas and form a foam 100 in-situ.

In another embodiment, the tip of the delivery catheter 200 is designed to prevent clogging by foam components. For example, in one embodiment, the catheter includes an inner hollow tube 220 that includes perforations, holes or the like 230 (as shown in FIG. 4a) and/or a mesh or other openings 240 (as shown in FIG. 4b) near the distal end thereof. Such features allow for the passage of gas and fluids from the delivery site during delivery of polymer through the distal end 210 of catheter 200. Such gas and fluids, which would otherwise increase the risk of clogging the catheter 200, may passively move out of the delivery space (e.g., an aneurysm sac) by a pressure gradient between the delivery space and ambient atmosphere, or a negative pressure may be applied to the proximal end of the inner hollow tube 220 to actively facilitate removal of gas from the delivery site. In an alternate embodiment, a second catheter may be used to actively or passively remove gas, water, and blood from the aneurysm sac.

In an alternate embodiment, the catheter 200 includes a one-way valve near the distal end 201 to prevent blood from wicking into the catheter and causing premature reaction of polymer therein. In some embodiments, the catheter 200 includes a pressure sensor on or near distal end 210 to indicate completion of foam delivery. Alternately, a pressure sensor is incorporated on or near the proximal end to measure pressure in the delivery lumen. This pressure should accurately reflect the pressure in the aneurysm sac when the user is not infusing material through the lumen and prior to completion of the crosslinking reaction.

Transport to an aneurysm site may be improved by providing formulations that can disperse within the sac before foaming and/or cross-linking Formulations have been generated that have a variety of reaction kinetics, as measured by cream time, gel time, and rise time. Cream time is defined as the time between the start of material mixing and the point at which fine bubbles begin to appear and the foam begins to rise. Gel time is defined as the time at which long "strings" of tacky material can be pulled away from the surface of the foam when the surface is contacted with the edge of a tongue depressor or similar instrument. Rise time is the time at which the foam stops expanding as observed visually. Overall reaction time can be adjusted by factors such as the hydrophilicity of the polymer formulation and amount of catalyst, and in certain embodiments is as short as 1 to 3 minutes, and in other embodiments, is as long as 10 minutes or longer. Example 4, below, contains further discussion on controlling kinetics by manipulating the composition of the material.

Foaming kinetics can be altered by adjusting the types and levels of catalysts and inhibitors used in the formulation. In general, the addition of weak acids such as acetic acid or citric acid may delay the start of foaming. The rate of foaming can be controlled by adjusting the relative levels of blowing and gelling catalysts.

Resistance of Blood Flow

Foams of the invention promote reduced blood flow when brought into contact with blood or sites of blood flow (e.g., Type II endoleaks). In preferred embodiments, foams of the invention have cell and pore structures with characteristics (including size, morphology, and tortuosity) that permit blood to enter the foam but which provide resistance to blood flow.

Pore density (defined as the number of open pores per unit area) can be controlled by adjusting the types and levels of ingredients in the formulation. In general, pore density can be altered by balancing the isocyanate index, surfactant levels, catalyst levels controlling both blowing and gelling rates, and the polyol viscosity. In many cases, subtle changes to a single ingredient level can drastically change the pore density.

In some cases, aneurysms continue to grow and remodel after placement of an endovascular graft. This growth can occur along the axis of the blood vessel leading to blood vessel dilatation at the proximal or distal ends which provided a seal against blood flow into the aneurysm sac. As this growth occurs, the seal may become compromised, the aneurysm sac pressurized and result in an increased risk of aneurysm rupture for the patient. The presence of the porous foam material in the aneurysm sac may lead to tissue ingrowth and ultimately stabilization of the aneurysm preventing aneurysm growth. For this purpose, the resulting in-situ foam preferably has an open cell structure and pore size conducive to tissue ingrowth (at least in the outer portion of the implant), and a resulting pore size preferably between 1 and 1000 microns and more preferably between 5 and 500 microns.

In some embodiments, a kit including one or more of the compositions previously discussed (e.g., a kit including a polymer formulation that can be foamed in-situ, a device comprising such a polymer formulation, a fluid for exposing to a polymer formulation to cause the foaming thereof and any other additive (e.g., external gas, second agent, etc.), a kit comprising a polymer formulation and a delivery system that can be used to create and/or deploy a polymer foam, or the like, is described. A "kit," as used herein, typically defines a package or an assembly including one or more of the compositions of the invention, and/or other compositions associated with the invention, for example, as previously described. In certain cases, some of the compositions may be constitutable or otherwise processable, for example, by the addition of a suitable solvent, other species, or source of energy (e.g., UV radiation), which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, fits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in certain cases, include different compositions that can be mixed to form a product. In certain embodiments, the kit may include physically separated chambers to hold the compositions, and a mechanism that is activated by a user or a machine for discharging the compositions and/or mixing them together. As a non-limiting example, the kit may include a dual barrel syringe having first and second chambers that contain first and second compositions, wherein the first and second chambers are physically separated, for example by a wall. In this example, the user may depress the plunger of the dual-barrel syringe to eject the first and second compositions from the first and second chambers. In certain embodiments, the kit also includes a static mixing nozzle, a dynamic mixing nozzle, an impeller, or a mixing chamber to permit the components to mix prior to or during discharge. In some embodiments, the kit includes a container or chamber within a delivery device that contains, or is configured to contain, saline or another fluid intended to cause the foaming reaction of the polymers delivered in accordance with the invention.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject, or to deliver the compositions of the invention into contact with bodily tissues to prevent, limit, or otherwise control bleeding or the flow of other bodily fluids. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In the compositions of the invention, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "alkoxy" refers to the group, —O-alkyl.
The term "aryloxy" refers to the group, —O-aryl.
The term "acyloxy" refers to the group, —O-acyl.
The term "aralkyl" or "arylalkyl", as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the 30 general formula: N(R')(R")(R''') wherein R', R", and R''' each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein, e.g., a drug or a peptide. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaruomatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like. The peptides described herein are inclusive of at least two amino acids connected by amide bond.

The present invention is further described with reference to the following non-limiting examples.

Example 1

An elastic silicone tube was used to simulate an aneurysm with two feeding vessels. This tube was placed over and sealed onto a rigid acrylic tube used to represent a stent-graft. The volume of the space between these two tubes was approximately 6 mL and was filled with water. A one-part polymer formulation was injected via syringe into this space, where it reacted and expanded in-situ to form a foam. This demonstrates that the foam can expand as desired into an anatomy analogous to an EVAR grafted aneurysm.

In this example, the foam was made from a polymer consisting of an isocyanate and a polyol. The formulation consisted of a mixture of the polymer, a diluent, a catalyst and a surfactant. In total, 1.4 mL of this mixture was injected to fill the space.

Example 2

In this example, a one-part polymer formula was delivered through a 90 cm, 5 Fr catheter into a silicone aneurysm model that was connected to a flow system. The aneurysm model was similar in size to a human abdominal aortic aneurysm and an endovascular stent-graft was placed across the aneurysmal segment (AneuRx®, Medtronic CardioVascular, Santa Rosa, Calif.). Within the aneurysmal segment, three silicone tubes were attached to mimic the inferior mesenteric artery and two lumbar arteries. These tubes were in fluid communication with the aneurysm. Static pressure heads were placed on all three tubes to simulate arterial pressure. The silicone aneurysm model was filled with water and connected to a flow loop comprised of silicone tubing and a peristaltic pump set to a flow rate of 1.6 L/min, similar to human cardiac output. The flow loop was placed in a water bath at 37 C, maintained by an immersion circulator. The total volume of the aneurysm was 145 mL and the volume of the aneurysm sac excluded by the stent-graft volume was approximately 100 mL. The formula in this example was formed from a mixture of a hydrophobic and a hydrophilic polymer; specifically, a hydrophobic, MDI-based, polymer was combined with a hydrophilic, TDI-based, strict polymer. A diluent was added to reduce the viscosity of the formulation to facilitate delivery through a catheter. In total, 20 mL of polymer was injected and the total aneurysm volume was 100 mL.

A 5 Fr catheter was placed into the space between the stent-graft and simulated aneurysm wall and 20 mL of a hydrophilic polymer was injected into this space. The polymer reacted in-situ to form a foam which expanded and filled more than 80% of the excluded aneurysm space without expanding the silicone aneurysm model or impinging on the stent-graft. Foam expansion into the simulated collateral vessels was up to about 2 cm. The in-situ formed foam made direct and intimate contact with the stent-graft.

Example 3

A polymer hydrophobic, MDI-based quasi polymer was deployed into two sheep models of abdominal aortic aneurysm and an in-situ forming foam injected via syringe to fill the excluded aneurysm space. The polymer was mixed with a diluent, a catalyst and a surfactant to optimize deliverability and reaction kinetics.

In the first model, an aneurysm was created in the sheep model using an anterior patch. In this model, a Dacron patch (HEMASHIELD®, Boston Scientific Corp., Natick, Mass.) was surgically inserted into the abdominal aorta. Doing so created a pocket of additional volume along the aorta. The sheep used was a 108 kg sheep with an abdominal aorta inner diameter of 9.2 mm. A 5 Fr catheter was advanced into the newly created aneurysm sac by angiography. To simulate a stent-graft excluding the aneurysm sac, a second 0.035" guidewire was inserted into the aorta to guide an 8 cm×10 mm DORADO® (CR Bard, Inc., Murray Hill, N.J.) balloon across the opening of the aneurysm sac. The balloon was dilated and contrast media was injected into the aneurysm sac to visualize the anatomy. An angiogram volume measurement determined the unpressured aneurysm to be 5.74 mL. The catheter was flushed with DMSO and 5.6 mL of the polymer (+0.4 mL dead space) was injected into the aneurysm sac. It reacted to form a foam in-situ, which filled the sac.

An endovascular aneurysm model was completed in a 70 kg sheep with an abdominal aorta inner diameter of 12.1 mm. To create the endovascular model a PALMAZ® (Cordis Corporation, Miami Lakes, Fla.) XL1040 metallic stent was balloon expanded to 18 mm or 1.5× the native vessel diameter. Doing so dilated the aorta to create an artificial aneurysm below the renal artery and above the iliacs and included at least one orifice for the lumbar arteries. A 5 Fr catheter was advanced to the expanded section of the aorta and a 13 mm VIABAHN® (W.L. Gore & Associates, Inc., Flagstaff, Ariz.) stent-graft was deployed into the vessel and addressed for blood flow. Contrast measurements indicated that the stent-graft did not exclude the aneurysm sac in a manner with clinical intent. To seal the mismatch at the distal end of the stent-graft, an esophageal balloon was dilated inside of the stent-graft to seal it against the vessel wall. Angiographic contrast was injected to verify isolation of the aneurysm and to identify the aneurysm volume excluded by the covered stent to be 2.71 mL. The catheter was flushed with DMSO and 0.6 mL of the polymer (+0.4 mL dead space) was injected into the aneurysm sac. The polymer reacted in-situ to form a foam, which did not penetrate or deform the stent-graft.

Example 4

In this example, two one-part polymer formulations with different reaction kinetics were injected into a model similar to that described in Example 2. In this example, the simple silicone aneurysm was replaced with a complex silicone aneurysm based on actual patient data. In addition, this complex model also had more than two-fold greater fill volume (212 mL vs 100 mL). Example 4A depicts a slow-foaming system, which required 10 minutes to achieve full rise, while Example 4B depicts a fast-foaming system, achieving full rise in only 3 minutes. Without wishing to be bound by theory, the hydrophilic polymer included in the faster example (4B) increases the overall polymer hydrophilicity, increasing water penetration into the polymer and increasing reaction speed through transport.

Example 4A Slow Kinetics

The formulation in this example was formed from a hydrophobic, MDI-based, polymer (formulation consisting of 100 parts hydrophobic polymer, 90 parts diluent, 10 parts catalyst, and 0.3 parts surfactant). In total, 40.5 mL of polymer was injected, and the total aneurysm volume was 212 mL. The foam expanded within the aneurysm after injection, achieving a full rise time after 10 minutes. After full rise, the model was removed from the water bath and photographed. Filling of the aneurysm space was estimated to be about 95%.

Example 4B Fast Kinetics

The formula in this example was formed from a mixture of a hydrophobic and a hydrophilic polymer. A hydrophobic, MDI-based, polymer was combined with a hydrophilic, TDI-based, strict polymer (formulation consisting of 90 parts hydrophobic polymer, 20 parts hydrophilic polymer, 80 parts diluent, 10 parts catalyst, and 0.3 parts surfactant). The foam expanded within the aneurysm after injection, achieving a full rise time after 3 minutes. After full rise, the model was removed from the water bath and photographed. Filling of the aneurysm space was estimated to be about 80%.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method for treating an aneurysm within a patient, the aneurysm characterized by a first end, a second end, and a surface between the first and second ends, said method comprising the steps of:
   placing a medical device within said aneurysm, said medical device comprising a structure having a first end, a second end, and an exterior surface between said first and second ends;
   delivering, with a catheter, a material between the exterior surface of said medical device and the surface of the aneurysm; and
   forming a foam from said material upon delivery between the exterior surface of said medical device and the surface of the aneurysm;
   wherein (a) said foam is formed by the reaction of said material with blood in situ and (b) the reaction includes the generation of a gas, said gas expanding a portion of the material into an interstitial area.

2. The method of claim 1, wherein said foam comprises polyurethane.

3. The method of claim 2, wherein said polyurethane is a poly(urethane urea).

4. The method of claim 1, wherein said foam is formed by the reaction of a multifunctional isocyanate and a polyol.

5. The method of claim 4, wherein said isocyanate is at least one of hexamethylene diisocyanate, toluene diisocyanate, methylene diphenyl diisocyanate, lysine isocyanate, isophorone diisocyanate, and mixtures thereof.

6. The method of claim 4, wherein said polyol is selected from the group consisting of polyethers and polybutadienes.

7. The method of claim 4, wherein said multifunctional isocyanate and said polyol are delivered between the exterior surface of said medical device and the surface of the aneurysm as separate components to form said foam.

8. The method of claim 4, wherein said multifunctional isocyanate and said polyol are delivered between the exterior surface of said medical device and the surface of the aneurysm as a mixture to form said foam.

9. The method of claim 1, wherein said foam comprises a visualization material.

10. The method of claim 1, wherein said foam further comprises at least one of a surfactant, a chain extender, a pore opener, a filler, a catalyst, a diluent, and a plasticizer.

11. The method of claim 1, wherein said foam contacts said surface of said aneurysm.

12. The method of claim 1, wherein said medical device comprises a graft.

13. The method of claim 1, wherein said medical device comprises a stent-graft.

14. The method of claim 1, wherein said medical device comprises a balloon.

15. The method of claim 1, wherein said delivering step comprises the steps of:
   placing a catheter between said first and second ends of said aneurysm; and
   introducing said material through said catheter.

16. The method of claim 15, wherein said catheter comprises a one-way valve.

17. The method of claim 1, wherein the material is a fluid comprising a prepolymer.

18. The method of claim 1, wherein the material is a fluid prepolymer.

19. The method of claim 1, wherein the material comprises a polysiloxane.

20. The method of claim 19, wherein the material comprises a multifunctional isocyanate and the gas is carbon dioxide.

* * * * *